(12) United States Patent
Wyman et al.

(10) Patent No.: US 6,461,373 B2
(45) Date of Patent: Oct. 8, 2002

(54) BIOINTERFERENCE SCREW FIXATION TECHNIQUE

(75) Inventors: Jeffrey Wyman; Reinhold Schmieding; Philip S. O'Quinn, all of Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 09/864,258

(22) Filed: May 25, 2001

(65) Prior Publication Data

US 2002/0010468 A1 Jan. 24, 2002

Related U.S. Application Data

(60) Provisional application No. 60/207,235, filed on May 26, 2000.

(51) Int. Cl.[7] .............................................. A61B 17/00
(52) U.S. Cl. .......................... 606/232; 606/73; 606/104
(58) Field of Search ............................ 606/232, 53, 60, 606/72, 73, 86–89, 96, 151, 213, 215–218, 104

(56) References Cited

U.S. PATENT DOCUMENTS

| | | | | |
|---|---|---|---|---|
| 5,632,748 A | * | 5/1997 | Beck, Jr. et al. | 606/89 |
| 5,643,320 A | * | 7/1997 | Lower et al. | 606/232 |
| 5,662,658 A | * | 9/1997 | Wentstrom, Jr. | 606/104 |
| 5,720,766 A | * | 2/1998 | Zang et al. | 606/232 |
| 5,733,307 A | * | 3/1998 | Dinsdale | 606/232 |
| 5,871,504 A | * | 2/1999 | Eaton et al. | 606/232 |
| 6,273,890 B1 | * | 8/2001 | Frazier | 606/73 |
| 6,319,270 B1 | * | 11/2001 | Grafton et al. | 606/73 |
| 6,355,053 B1 | * | 3/2002 | Li | 606/232 |
| 6,355,066 B1 | * | 3/2002 | Kim | 606/232 |

* cited by examiner

Primary Examiner—Gloria M. Hale
(74) Attorney, Agent, or Firm—Dickstein Shapiro Morin & Oshinsky, LLP

(57) ABSTRACT

Endosteal fixation of a ligament graft with an interference fixation device installed in a retrograde manner is disclosed. An interference screw is installed at the top of the tibial tunnel, through the tibial plateau, in a procedure for ACL reconstruction. The interference screw is fitted with a length of suture for pulling the screw onto a driver placed through the tibial tunnel. The suture is secured to the screw using a knot, an adhesive, insert molding, and equivalents. The suture extends beyond the leading tip of the screw a sufficient length to allow the screw to be passed into the joint by pulling on the suture exiting the tibial tunnel. A driver fits into a drive opening in the leading front end of the screw. Turning the driver advances the screw in a retrograde manner into the tunnel. Accordingly, interference fixation of the graft near the tibial plateau is provided, thereby eliminating graft abrasion at the tibial plateau tunnel opening.

7 Claims, 2 Drawing Sheets

US 6,461,373 B2

BIOINTERFERENCE SCREW FIXATION TECHNIQUE

This application claims the benefit of U.S. Provisional application Ser. No. 60/207,235 filed May 26, 2000.

BACKGROUND OF THE INVENTION

1. Field of the Invention

The present invention relates to interference screw fixation of replacement ligament grafts, and more particularly to methods and apparatus for retrograde placement and installation of an interference screw for graft fixation in a bone tunnel.

2. Brief Description of the Related Art

Methods of anterior cruciate ligament (ACL) reconstruction using interference screw fixation are described in U.S. Pat. Nos. 5,211,647 and 5,320,626, the entire disclosures of which are incorporated herein by reference. In general, these methods of tenodesis involve drilling a tunnel through the tibia, drilling a closed tunnel (socket) into the femur, inserting a substitute ACL graft into the tunnels, and securing the grafts to the walls of the tibial and femoral tunnels using interference screws or the like. Accurate positioning of the tibial and femoral tunnels requires a drill guide, such as those disclosed in U.S. Pat. Nos. 5,269,786 and 5,350,383, which also are incorporated herein by reference.

One drawback of the described tenodesis methods is that the ligament graft is secured only at the bottom of the tibial tunnel. The graft is not secured at the top end of the tibial tunnel. Consequently, the graft is free to move from side to side, resulting in a "windshield wiper" effect, during which the graft abrades against the upper rim of the tibial tunnel, shortening the life of the ACL repair.

U.S. Pat. No. 5,603,716 to Morgan et al. discloses a technique for ACL reconstruction that avoids the above-noted problem of graft abrasion. The method disclosed by Morgan et al. requires forming two closed-ended sockets, one in the tibia and the other in the femur.

Accordingly, the need exists for a method of ACL reconstruction that provides anatomical graft fixation at the tibial plateau, and without the need for forming two separate bone sockets.

SUMMARY OF THE INVENTION

The present invention overcomes the disadvantages of the prior art, such as those noted above, by providing methods and apparatus for endosteal fixation of a ligament graft using an interference fixation device that is installed in a retrograde manner. In a preferred embodiment, anterior cruciate ligament (ACL) reconstruction is performed using an interference screw installed in a retrograde manner through the tibial plateau to secure an ACL graft at the top of the tibial tunnel.

The interference fixation screw is fitted with a length of suture to provide a means for pulling the screw into the tibial tunnel through the tibial plateau. The suture preferably passes through the length of the screw and engages the trailing end of the screw. The suture is secured to the screw using at least one of a knot, an adhesive, insert molding, and equivalent securing methods. The suture extends beyond the leading tip of the screw a sufficient length to allow the suture to be passed through the tibial tunnel and to be grasped for pulling the screw into the top opening of the tunnel. The screw and suture preferably are bioabsorbable.

A driver for the screw fits into a drive opening in the leading end of the screw. Preferably, the driver is cannulated to accept the length of suture extending from the bottom opening of the tibial tunnel, and has means for grasping the suture to assist the surgeon in pulling the interference screw into the top opening of the tibial tunnel.

According to a preferred method of the present invention, after the ligament graft has been placed in the tibial tunnel, the suture extending from the interference screw is fed into the joint cavity, into the top, tibial plateau opening of the tunnel, and down through the tibial tunnel to exit at the anterior surface of the tibia. The free end of suture exiting the anterior surface of the tibial tunnel preferably is captured within the cannulated driver. Alternatively, a knot could be formed on the end of the suture to secure the suture to the driver, or a separate suture puller could be used within the scope of the present invention.

Drawing on the suture using the driver at the anterior opening of the tibial tunnel pulls the interference screw into the joint cavity in a retrograde fashion. The knee joint is positioned to allow the end of the screw to be manipulated into the top opening of the tibial tunnel, with the screw being pivoted within the joint cavity to align axially with the tunnel and the driver.

With the screw being drawn into a position of alignment with the tunnel, the driver is advanced into the tibial tunnel. Pulling on the suture retains the screw in position for engagement with the driver by applying tension to the suture in the direction opposing driver insertion.

Once the driver has engaged the screw, turning the driver causes the screw to advance, or "back in" to the tunnel in retrograde fashion. Using a right-threaded screw, a surgeon will turn the screw counter-clockwise. In an alternative embodiment, the screw has reverse threads, so that turning the driver clockwise advances the screw into the tunnel. The screw is turned into the tunnel until the back end of the screw is substantially flush with the tibial plateau, and has been installed to a depth sufficient to provide interference fixation of the graft at the top of the tunnel.

The driver is disengaged from the screw, and excess suture is removed.

Other features and advantages of the present invention will become apparent from the following description of the invention which refers to the accompanying drawings.

DETAILED DESCRIPTION OF THE PREFERRED EMBODIMENTS

Figure 3:
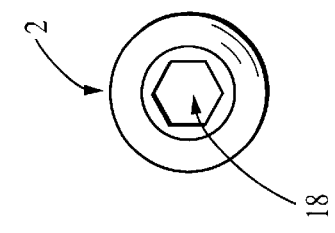
FIG. 3 is a proximal end view of the screw of FIGS. 1 and 2.
Figure 2:
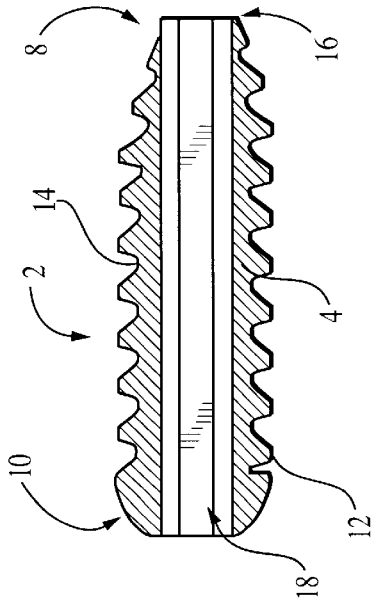
FIG. 2 is a cross-sectional elevation of the screw of FIG. 1.
Figure 1:
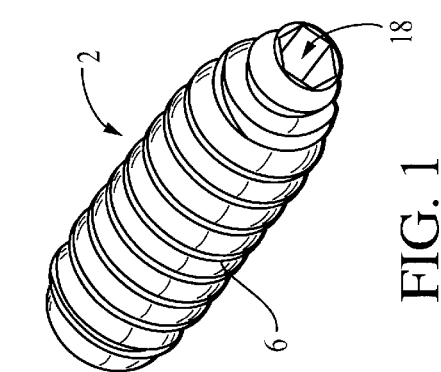
FIG. 1 is a perspective view of a bio-tenodesis screw according to the present invention.

Referring initially to FIGS. 1–3, a bioabsorbable interference screw 2 for tenodesis of an anterior cruciate ligament graft is shown. Body 4 of the screw 2 features a continuous thread 6 provided substantially along the length of the body from a blunt front end 8 to a rounded back end 10. The thread preferably has flattened crests 12 and flattened troughs 14 to obviate ligament graft damage by the screw threads and enhance graft fixation.

The cannulated body 4 tapers toward the front end 8 to terminate in a blunt tip 16. The taper eases entry of the screw into the tibial tunnel according to the preferred method of ligament graft fixation described further below. The blunt tip 16 of the screw prevents damage of the ligment graft during insertion of the screw. The rounded back end 10 of the screw minimizes abrasion and wear of the installed ligament graft. Cannula 18 formed through screw body 4 has a hexagonal shape for engaging a driver described below. Preferably, cannula 18 is straight, although a tapered cannula could be used. The hexagonal shape of cannula 18 is shown clearly in FIG. 3. The preferred screw is 23 mm long, and is supplied in various diameters.

Figure 4:
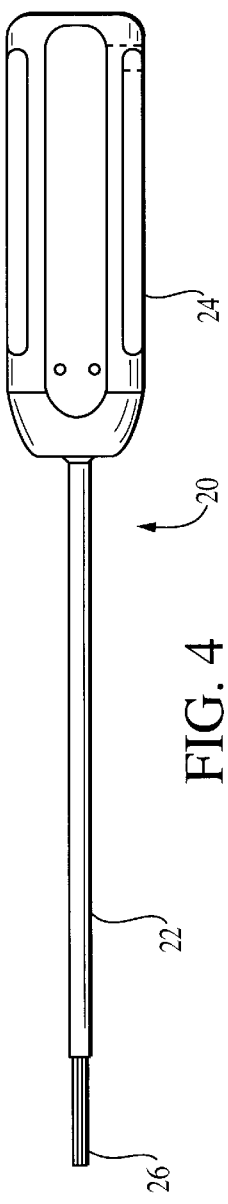
FIG. 4 is an elevation of a driver for the screw of FIGS. 1–3 according to the present invention.
Figure 5:
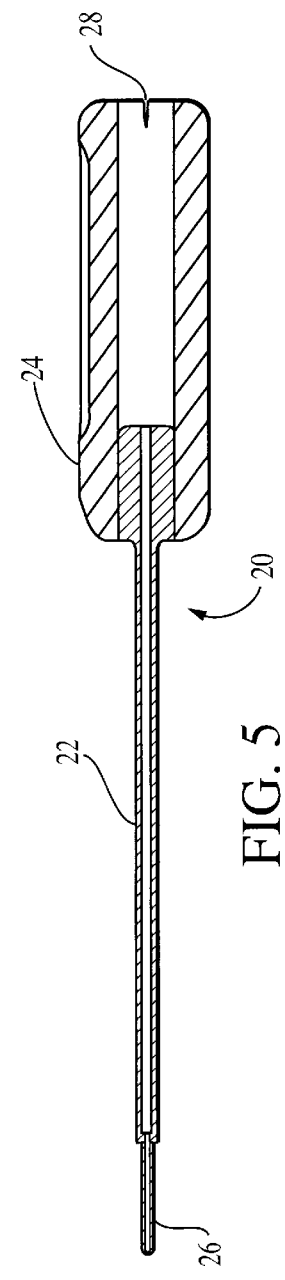
FIG. 5 is a cross-sectional plan view of the driver of FIG. 4.

Referring to FIGS. 4 and 5, a driver 20 for installing the interference screw is shown. Driver 20 includes a cannulated shaft 22 secured permanently to a cannulated handle 24. A drive tip 26 formed at the distal end of shaft 22 has a straight, hexagonal shape conforming to cannula 18 of screw 2. At the proximal end of the handle, notches 28 are provided on either side for securing suture.

Figure 6:
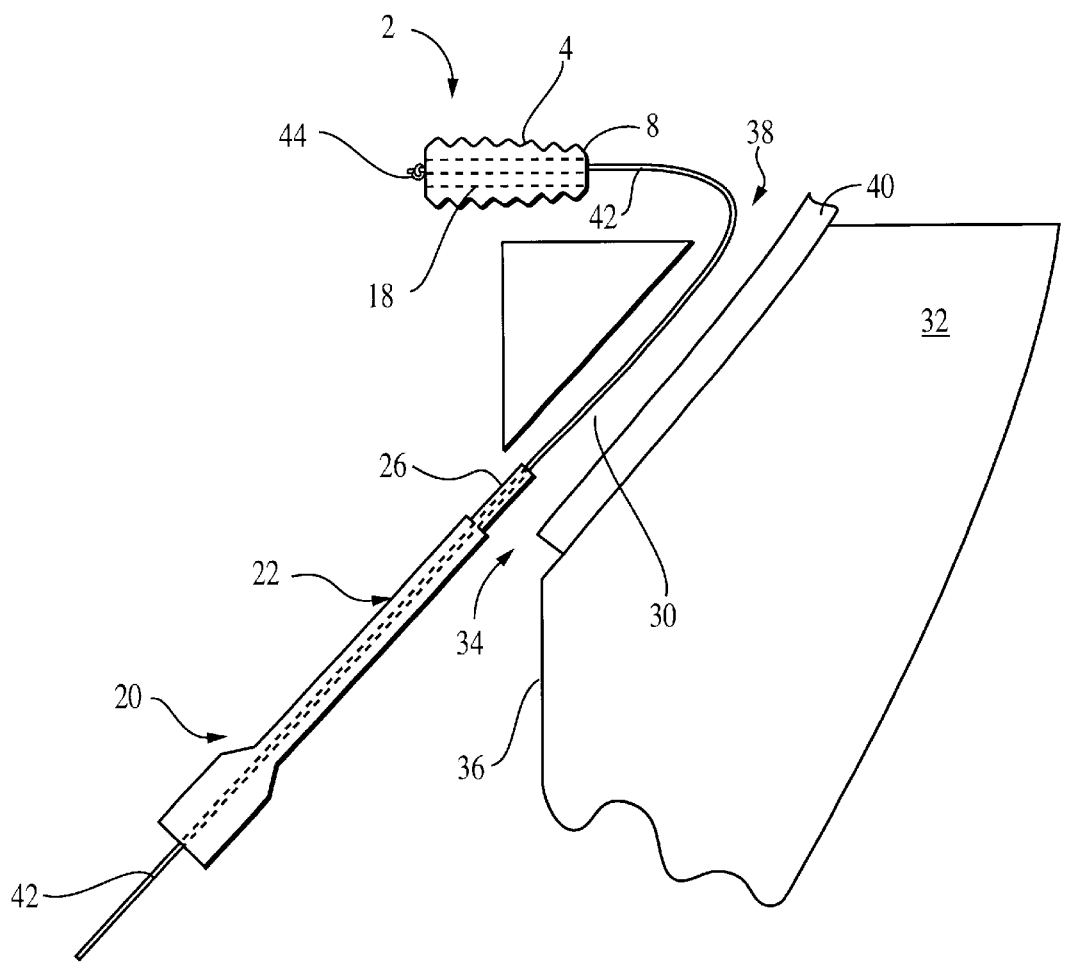
FIG. 6 schematically illustrates fixation of an ACL graft using the retrograde biointerference screw of the present invention.

A method of ACL tenodesis according to a preferred embodiment of the present invention includes forming a tunnel 30 in a tibia 32, as shown in FIG. 6. The tunnel is formed with a diameter appropriate for interference fixation based on the size of the selected screw 2. Tunnel 30 ascends at an angle posteriorly from a bottom opening 34 at an anterior tibial surface 36 toward an upper opening 38 at the tibial plateau. The lower end of an ACL graft 40 is inserted into the tunnel through the tibial plateau.

The length of suture 42 passing through interference screw 2 is secured at the back end of the screw using a knot 44, for example. Screw 2 is inserted into the joint and through the tunnel 30 so that a free end of the suture exits the bottom opening 34. Suture passing instruments as are known can be utilized.

The free end of the suture is used to draw screw 2 toward the tibial opening 38, either by hand or using driver 20 by threading the suture into the driver 20 and securing the suture in notches 28, for example. With the knee joint distended, the screw 2 is manipulated into the tibial plateau opening 38 and pivoted into axial alignment with the tunnel 30. Driver 20 is advanced into the tunnel 30 to achieve engagement with screw 2. Turning the screw with the driver advances the screw into the tunnel 30 in a retrograde manner. Screw insertion is continued until the back end 10 of screw 2 is substantially flush with the tibial plateau and the graft 40 is secured sufficiently within the tunnel. The driver 20 and any excess suture 4 is removed from the tunnel to complete this portion of the procedure.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An interference screw comprising:

a cannulated body having a length, a leading tip and a trailing end;

a screw thread formed on the body; and a length of suture secured to the body for pulling the screw into a joint, the suture engaging the trailing end of the screw and extending along the body of the screw and beyond the leading tip of the screw a sufficient length to allow the suture to be passed through a bone tunnel for pulling the leading tip of the screw onto a screwdriver for retrograde insertion by rotation of the screw into the bone tunnel.

2. A method of endosteal fixation comprising the steps of:

positioning a ligament graft in a bone tunnel;

passing a length of suture extending from a leading tip of a biointerference screw through the bone tunnel in a first direction; and drawing on the suture in the first direction to position the screw at one end of the bone tunnel and to secure the leading tip of the screw onto a driver for retrograde turning of the screw into the bone tunnel.

3. The method of claim 2, further comprising the steps of engaging the screw with the driver, and rotating the screw to advance the screw into the tunnel.

4. A method of anterior cruciate ligament reconstruction, the method comprising the steps of:

forming a tibial tunnel between an anterior tibial surface and the tibial plateau, thereby forming an opening in the tibial plateau;

placing a ligament graft in the tibial tunnel;

feeding a length of suture extending from and attached to an interference screw down through the tibial tunnel by way of the opening in the tibial plateau, a free end of the suture exiting the tibial tunnel at the anterior tibial surface;

drawing on the free end of the suture exiting the tibial tunnel to pull the interference screw into the joint cavity;

manipulating a leading end of the screw into the top opening of the tibial tunnel, the screw being positioned within the joint cavity to align axially with the tunnel;

advancing a driver up into the tibial tunnel to engage the screw with the driver; and turning the driver to advance the screw in a retrograde fashion down into the tunnel.

5. The interference screw of claim 1, further comprising a drive opening in the leading tip of the cannulated body.

6. The method of claim 3, wherein the step of engaging the screw with the driver includes inserting the driver into the tunnel in a second direction opposite to the first direction.

7. The method of claim 4, wherein the screw has a trailing end, and the screw is advanced into the tunnel until the trailing end is flush with the tibial plateau.

* * * * *